United States Patent [19]

Hammarberg et al.

[11] Patent Number: 5,544,519
[45] Date of Patent: Aug. 13, 1996

[54] METHOD AND APPARATUS FOR MEASURING THE FLOW RESISTANCE OF A CATHETER IN AN IMPLANTED MEDICATION INFUSION SYSTEM

[75] Inventors: Bjoern Hammarberg, Solna; Jan Rosen, Grillby; Bruno Slettenmark, Jaerfaella, all of Sweden

[73] Assignee: Siemens Elema AB, Solna, Sweden

[21] Appl. No.: 326,199

[22] Filed: Oct. 20, 1994

[30] Foreign Application Priority Data

Oct. 22, 1993 [SE] Sweden ................... 9303484

[51] Int. Cl.$^6$ .................. G01M 19/00; B01L 3/02
[52] U.S. Cl. .................. 73/37; 73/54.07; 604/111
[58] Field of Search .............. 73/864.13, 864.16, 73/37, 54.07; 604/111

[56] References Cited

U.S. PATENT DOCUMENTS

| | | | |
|---|---|---|---|
| 3,945,254 | 3/1976 | Rebold | 73/425.6 |
| 3,954,014 | 5/1976 | Andrews, Jr. et al. | 73/425.6 |
| 4,196,730 | 4/1980 | Wilson | 128/214 |
| 4,383,531 | 5/1983 | Panagiotopulos | 604/114 |
| 4,710,177 | 12/1987 | Smith et al. | 604/185 |
| 4,721,123 | 1/1988 | Cosentino et al. | 134/57 R |
| 4,741,736 | 5/1988 | Brown | 604/134 |
| 5,024,668 | 6/1991 | Peters et al. | 606/194 |
| 5,092,161 | 5/1992 | Jenkins et al. | 73/37 |
| 5,135,488 | 8/1992 | Foote et al. | 604/97 |
| 5,192,272 | 3/1993 | Faure | 604/141 |
| 5,201,753 | 4/1993 | Lampropoulos et al. | 606/192 |
| 5,279,147 | 1/1994 | Bertini et al. | 73/40 |
| 5,300,027 | 4/1994 | Foote et al. | 604/100 |
| 5,425,713 | 6/1995 | Taylor et al. | 604/100 |
| 5,431,629 | 7/1995 | Lampropoulos et al. | 604/100 |

FOREIGN PATENT DOCUMENTS

0519765  12/1993  European Pat. Off. .

OTHER PUBLICATIONS

"Pompes Implantables À Insuline: Intérêt d'un 'port d'accès latéral' pour le diagnostic et le traitement des obstructions di cathéter," Selam, Infusystémes, vol. 6, pp. 30–32 (1989).

*Primary Examiner*—Thomas P. Noland
*Assistant Examiner*—Jay L. Politzer
*Attorney, Agent, or Firm*—Hill, Steadman & Simpson

[57] ABSTRACT

In a method for measuring the flow resistance of a catheter in an implanted medication infusion system, the system having a medication reservoir and a pump that conveys the medication from the reservoir into the patient through a catheter connected to the discharge of the pump via a one-way valve, and having a rinsing input for direct access to the catheter disposed upstream of the catheter and downstream of the pump, the time required in order to pump a pre-determined liquid volume through the catheter via the rinsing input at a predetermined pressure is measured. In a device for such a flow check, a testing device is provided for connection to the rinsing input, which pumps a predetermined liquid volume through the catheter via the rinsing input at a predetermined pressure. Measuring sensors are provided for supplying signals from which the time required for pumping this liquid volume can be determined.

11 Claims, 2 Drawing Sheets

METHOD AND APPARATUS FOR MEASURING THE FLOW RESISTANCE OF A CATHETER IN AN IMPLANTED MEDICATION INFUSION SYSTEM

BACKGROUND OF THE INVENTION

1. Field of the Invention

The present invention is directed to a method for measuring the flow resistance of a catheter in an implanted medication infusion system for medication of the type having a medication reservoir and a pump that conveys the medication from the reservoir through a catheter connected to the discharge of the pump via a one-way valve into the patient, and having a rinsing input (port) for direct access to the catheter disposed upstream of the catheter and downstream of the pump. The invention is also directed to an apparatus for measuring flow resistance.

2. Description of the Prior Art

A problem associated with implanted infusion systems for delivering medications in the form of a liquid, for example an insulin solution, through a catheter to a patient is that flow impediments can arise in the catheter. Such flow impediments arise particularly in the catheter or in the area of the catheter opening. These flow impediments can occur because, for example, medication or body fluid leaking in a backward direction, or both of these fluids, can form deposits at the inside wall of the catheter. When these deposits become too thick, the delivery of medication is prevented. Flow impediments in the catheter, further, can arise when body tissue grows over or into the opening of the catheter.

It is desirable that the initial formation of such flow impediments in the catheter be discovered as early as possible so that measures that prevent a partial or total blockage of the medication delivery can be undertaken. Some form of measuring the catheter flow function is therefore desirable.

Heretofore, the catheter has been rinsed clean without making any flow measurement by inserting a syringe of a suitable size, for example 20 ml, by penetrating through the skin and through the septum of the rinsing input. The catheter is rinsed by manually discharging the contents of the syringe. The hope has been that the catheter flow function would thereby be improved. Such catheter rinsing is implemented "blind," i.e., without definite knowledge that rinsing was really necessary since no flow measurements were made. This is unsuitable since there are a number of reasons why an unnecessary rinsing of the catheter should be avoided. Further, no reliable information has been obtained in such known procedures as to whether the rinsing had the intended effect, or what, if any, modification of the flow function was achieved. The only "feedback" is that the syringe operator may possibly receive a subjective feeling that a blockage was dissolved.

An article entitled "Pompes Implantables À Insuline: Intér êt d'un des 'port d'acces lateral pour le diagnostic et le traitement des obstructions di cathéter," Selam appearing in Infusystemes, Vol. 6, pp. 30–32 (1989), discloses a method for indicating a blockage in a catheter by pressuring the catheter and registering the chronological decay of the pressure using a pressure transducer connected to the rinsing input, the pressure transducer being connected to a plotter. The result is compared to the shape of the decay curve of a new (unblocked and intact) catheter. Air bubbles in the syringe, in the pressure transducer and in the rinsing input cannot be entirely avoided, and this yields decay times of different length for the same catheter when the measurement is repeated. The measured results obtained with this technique are of a qualitative and not of a quantitative nature.

SUMMARY OF THE INVENTION

An object of the present invention is to obtain a quantitative measurement of the catheter flow function in implantable infusion systems in a way that is risk-free for the patient.

The above object is achieved in accordance with the principles of the present invention in a method for measuring the flow resistance of a catheter in an implanted medication infusion system, wherein the system included a medication reservoir and a pump which conveys the medication from the reservoir to the patient through the catheter connected to the output of the pump via a one-way valve, and the system including a rinsing input for direct access to the catheter disposed upstream of the catheter and downstream of the pump, the method including the steps of introducing a predetermined liquid volume into the catheter via the rinsing input at a predetermined pressure, and measuring the time required for pumping the predetermined liquid volume through the catheter.

The above object is also achieved in an apparatus for implementing the above method, which includes a test device connectable to the rinsing input which pumps the predetermined liquid volume into the catheter via the rinsing input at the predetermined pressure, and measuring means are provided for measuring the aforementioned time required for pumping this predetermined liquid volume.

The invention consequently enables a quantitative measurement of the flow resistance in an implanted catheter connected to an implanted infusion system, in which a direct access to the catheter in the form of a rinsing input that is disposed upstream of the catheter and downstream of the infusion pump is present. The measurement itself is that of the time required for pumping a predetermined liquid volume through the catheter at a predetermined pressure. This pressure can be chronologically varied or can be constant. The time required for emptying the pre-determined liquid volume is a measure of the degree of constriction in the implanted catheter. It is therefore important to ensure that the means for connecting the implanted infusion system to the testing equipment do not significantly influence the flow resistance. The measurement can be implemented by employing sterile disposable details.

Poiseuille's formula provides a simple, quantitative relationship between the inside diameter and the length of the catheter, or the inside diameter and length of occlusions in the catherer, if present. The inventors have recognized that the flow resistance of the catheter can be ascertained from the aforementioned measured time. This is because, according to Poiseuille's formula, the volume per unit of time of a fluid flowing through a cylinder is dependent (among other things) on the inner diameter and length of the cylinder. Occlusions which reduce the inner diameter thus reduce the flowing volume per time unit, and thus by monitoring the time required for a given volume of fluid to flow through the cylinder, one obtains an indication of the degree to which the cylinder (catheter) has become occluded. It can thereby be determined when the constriction is so significant that it influences the normal insulin flow and influences what is referred to as the bolus flow, and it is then a simple matter to determine when a rinsing should be implemented whenever the measured time reaches a prescribed value (duration).

According to Poiseuille's formula, the following is valid for a laminar flow through a narrow, horizontally oriented circular cylinder having the radius R and the length l:

$$dV/dt = \pi R^4 / 8\eta \cdot \Delta p / l$$

wherein Δp is the pressure difference between the ends of the cylinder, dV/dt is the volume flowing out per unit of time and n is the dynamic viscosity of the liquid. For the current purposes, the flow can be considered with a high degree of accuracy to be laminar.

After a rinsing has been carried out, the time measurement can advantageously be undertaken again in order to obtain a quantitative measure of the modification that was achieved.

Slow variations in the flow function of the catheter can be tracked on the basis of regular measurements in conformity with the invention, for example in combination with the filling of the system at every other time, i.e. every other month in practice, and the catheter function can be predicted and measures for rinsing the catheter clean can thus be planned. The occurrence of air bubbles in the syringe and in the rinsing input to a "normal" extent continues to have only an insignificant influence on the precision of the method.

Tests have shown that the method and the arrangement of the invention are extremely sensitive and that modifications in the flow function of the catheter are indicated in a simple manner long before these modifications have an influence on the delivery of the medication, and consequently long before they have clinical significance.

In an embodiment of the invention, the pre-determined pressure intended for the measurement is selected lower than the normal pump pressure developed by the internal pump of the infusion system for conveying medication from the reservoir to the patient through an open (unoccluded) catheter. This is important because it would be undesirable if the pressure used to make the measurement for occlusions were to modify the condition of the catheter, such as may occur if the measurement pressure were so high as to dislodge or diminish an existing occlusion. The measurement is intended to obtain information about the catheter as the catheter existed before the measurement. It is important in case of a therapy malfuntion to identify the cause or the causes of why the therapy functioned unsatisfactorily and if the measurement itself altered the pre-existing catheter condition, the reason for the malfunction may then be undiscernible. The present invention consequently avoids the measurement itself altering the pre-existing condition of the catheter, as occurs in the known technique se forth in the aforementioned article by Selam and Irvine.

In another embodiment of the apparatus of the invention, the testing instrument is connected to the rinsing input via an external connecting line and via a cannula that is dimensioned such that the influence thereof on the measured time is insignificant.

Tests of this embodiment with cannulae having a flow resistance less than 5% of the flow resistance of the catheter and with connecting lines having a flow resistance which is less than 0.5% of the flow resistance of the catheter have been carried out.

DESCRIPTION OF THE PREFERRED EMBODIMENTS

Figure 1:
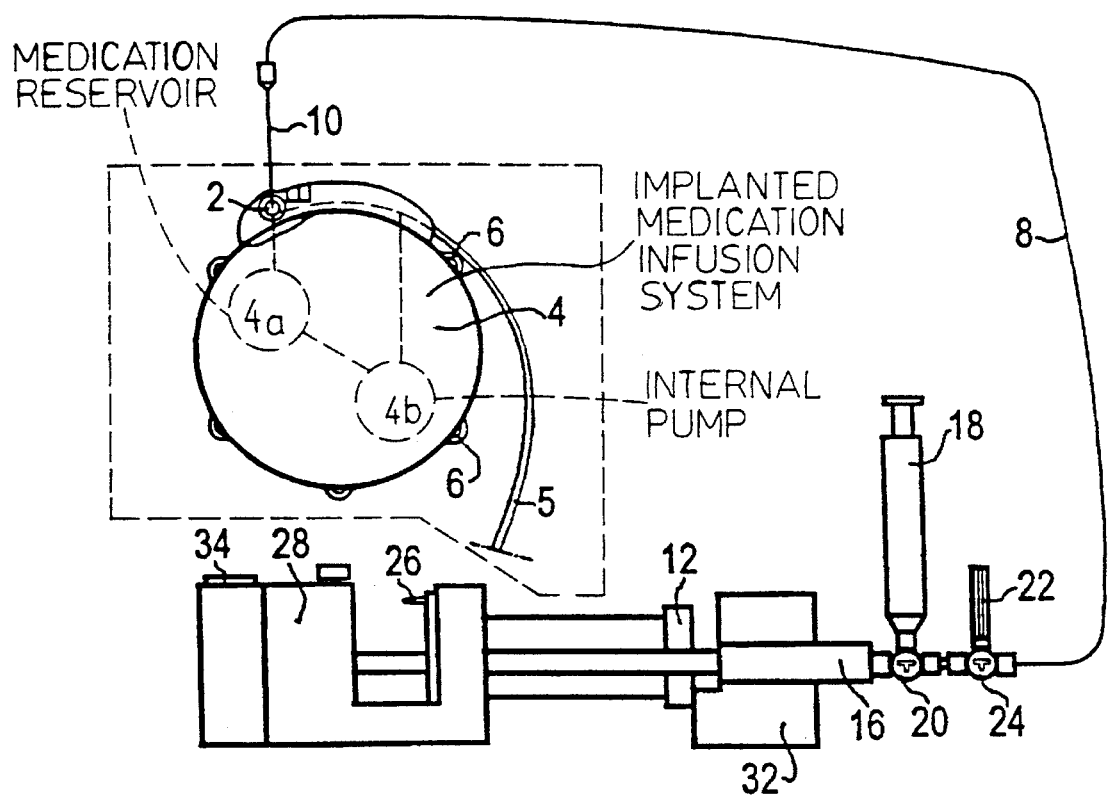
FIG. 1 shows an embodiment of the apparatus of the invention that is connected to an implantable infusion device or infusion system.

FIG. 1 shows an overview of an apparatus of the invention that is connected to an implantable infusion system or infusion device 4. The dashed line in FIG. 1 schematically indicates that the infusion device 4 is implanted in a patient, with other components of FIG. 1 being extracorporeal. The infusion device 4 includes a medication reservoir 4a and a internal pump 4b, the internal pump 4b conveying the medication from the reservoir 4a through a catheter 5 connected to the discharge of the pump 4b via a one-way valve (not shown) and into the patient. Means for subcutaneously fastening the infusion device 4 after implantation, such as suture eyelets 6, are provided at the outside of the housing of the infusion device 4. The device of the invention is connected to the rinsing input 2 of the infusion device 4 via a connecting line 8 and via a cannula 10. The cannula 10 is provided for the purpose of penetrating into the rinsing input through the skin of the patient and through a septum that covers the rinsing input.

Figure 2:
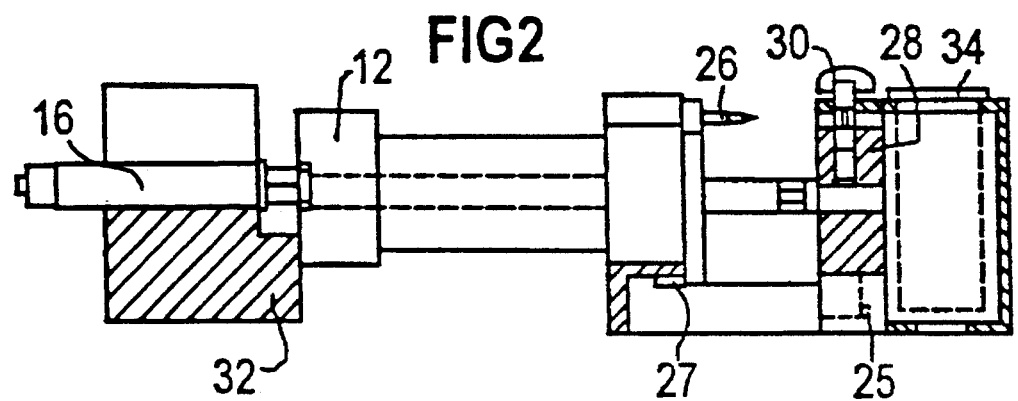
FIGS. 2–4 illustrate the testing instrument in combination with the device of the invention, shown in views from three different sides, partly in section, with the piston initially in its front position with the piston spring in a relaxed condition in FIGS. 2 and 3, and with the piston in a retracted position with the spring in a compressed condition in FIG. 4.
Figure 3:
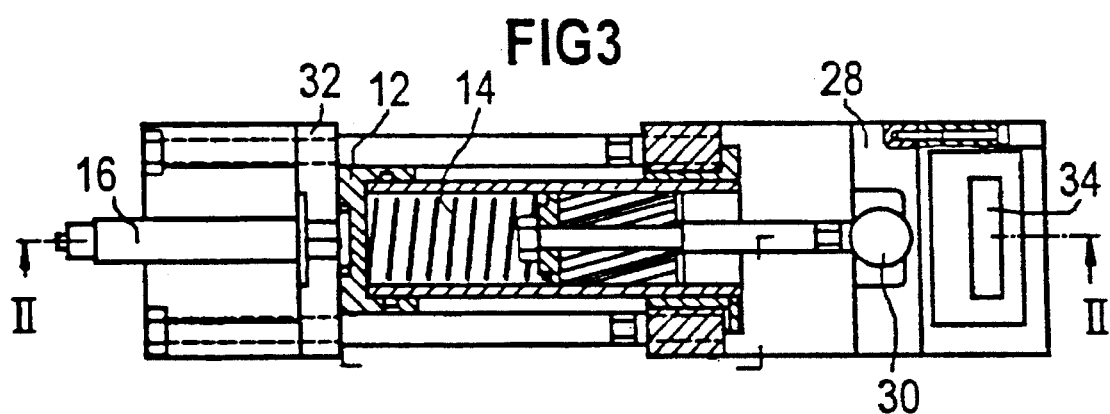
Figure 4:
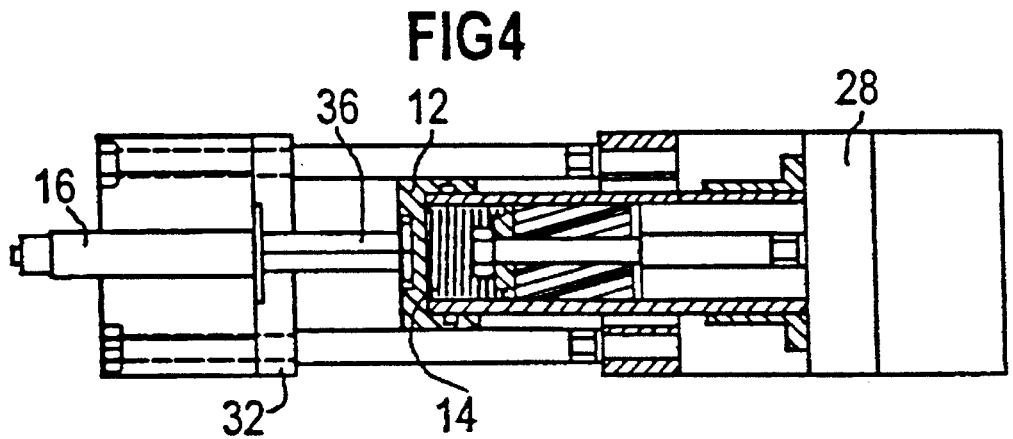

A testing device in combination with the apparatus of the invention is shown in FIG. 1 and in three different side views in FIGS. 2–4. The testing device has a movable piston 12 in which one or more springs 14 that exert an essentially constant pressure on the piston when released are arranged. The size of the force is matched to the syringe employed-see below-and can, after reduction by internal losses due to friction in the syringe etc., typically produce a liquid pressure in the syringe of the order of magnitude of 0.5 bar.

The force acting at the piston 12, of course, can be produced in some other fashion, for example using one or more pneumatic springs.

A catheter in which a sterile, non-reusable syringe 16 can be clamped fast is provided at the one end of the testing device. The syringe 16 preferably has a volume of 2 ml and is filled with a liquid, for example with an "insulin dilution buffer", that is harmless for the patient.

As shown in FIG. 1, a ten-ml syringe 18 is connected to the output of the testing device via a three-way valve 20. This syringe 18 is filled with the liquid employed and serves as reservoir. Accordingly, the syringe 16 is filled by the syringe 18 before the measuring procedure, and the syringe 18 can also be used for rinsing the catheter clean after the measuring procedure of the implanted catheter.

Further, an external pump stroke indicator 22 is connected via another three-way valve 24. The external pump stroke indicator 22 senses the pressure elevations at each pump stroke of the internal pump 4b of the infusion device when the cannula has been properly introduced into the rinsing input 2. The proper introduction of the cannula 10 into the rinsing input 2 is thus verified with this indicator. The external pump stroke indicator 22 can be a pressure transducer or a liquid filled cylinder containing a sinker member that is disclosed in Swedish Patent Application 9303485-8, corresponding to co-pending U.S. application Ser. No. 08/326,209 filed Oct. 20, 1994 ("External Pump Stroke Indicator for Use With An Implanted Medication Infusions System," Rosen), the teachings of which are incorporated herein by reference.

A closure splint 26 that is secured to the piston 12 is provided in order to block the piston in the spring-compressed position, i.e. in the piston position at the extreme left in FIG. 1 and in the piston position at the extreme right in FIGS. 2–4. This closure splint 26 can be locked at the left in FIG. 1 and at the right in FIGS. 2 and 4 in a hole present in the block 28. In order to start the course of the measurement, the closure splint 26 is released from the blocked position by pressing the closure key 30.

Two signal-emitting devices 25 and 27, for example, microswitches that are attached along the motion path of the piston 12, are provided for registering the time required for emptying the syringe 16. One signal-emitting device 25 is arranged at the same block 28 of the device as the closure key 30 and the other signal-emitting device 27 is arranged at that part of the device that holds the piston 12 in its front final position. This may be seen from FIG. 2. The signal-emitting devices 25 and 27 are switched on and off at the final positions of the piston 12, and the conveying time from the starting position to the final position is displayed on a display 34.

The operation of the apparatus of the invention is as follows:

The piston 12 is placed in a position which compresses the spring 14 and is held in that position with the closure splint 26. The syringe 16 is filled with liquid from the syringe 18 via the valve 20. In order to be certain that the syringe 16 is filled at the end of the filling procedure, a check should be made to insure that the syringe piston 36 lies against the piston 12. This initial position is shown in FIG. 4.

The closure splint 26, which holds the piston in the spring-compressed position, is released by pressing the closure key 30, and the piston 12 moves with a constant pressure from right to left in FIGS. 2-4, whereby the content of the syringe 16 is emptied into the rinsing input 2 of the infusion device 4 through the valves 20 and 24, the connecting line 8 and the cannula 10. into the rinsing input 2 of the infusion device 4 through the valves 20 and 24, the connecting line 8 and the cannula 10.

The time required for emptying the syringe 16 is registered with the aforementioned signal-emitting devices 25 and 27 that are arranged along the piston path and this time is presented at the display 34. The time provides a measure of the degree of flow delay in the implanted catheter according to Poiseuille's formula, with the condition that the external connecting line 8 and the cannula 10 are selected such that their influence on the measured time is insignificant, as already mentioned. If the implanted catheter has a length of 250 mm and having a diameter of 0.3 mm, then an external connecting line having a length of 1000 mm with a diameter of 1.0 mm as well as a cannula having a length of 24 mm and a diameter of 0.5 mm can be suitable.

The time required for emptying the syringe 16 measured by the device of the invention is compared to the emptying time of a new and entirely open (unoccluded) catheter whose values are listed in a table. Based on the time required for emptying the syringe 16 measured with the invention, a decision can thus be made whether the implanted catheter must be rinsed or need not be rinsed. When a rinsing must be implemented, this ensues with the syringe 18 after the valve 20 has been switched. After the rinsing, a second measurement of the time required for emptying the syringe 16 can ensue in order to determine whether the rinsing had the desired effect on the implanted catheter.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for extracorporeally measuring flow resistance in a catheter in a completely implanted medication infusion system, said implanted medication infusion system including a medication reservoir and an internal pump for conveying the medication from the reservoir in vivo via said catheter to a specified site within the patient, said catheter being connected to an output of said internal pump via a one-way valve, and said system including a rinsing input providing access to said catheter, said rinsing input disposed upstream of said catheter and downstream of said internal pump, said method comprising the steps of:

percutaneously introducing, from an extracorporeal location, a predetermined volume of liquid at a predetermined pressure into said implanted catheter via said rinsing input; and measuring a time required for all of said predetermined volume of liquid to pass through said implanted catheter via said rinsing input at said predetermined pressure.

2. A method as claimed in claim 1 comprising the additional steps of rinsing said implanted catheter and wherein the step of measuring a time required for all of said predetermined volume of liquid to pass through said implanted catheter via said rinsing input at said predetermined pressure comprises measuring said time required for all of said predetermined volume of liquid to pass through and implanted catheter via said rinsing input before rinsing said implanted catheter and measuring said time required for all of said predetermined volume of liquid to pass through and implanted catheter via said rinsing input after rinsing said implanted catheter.

3. A method as claimed in claim 1 wherein said internal pump conveys said medication through said implanted catheter at a medication pumping pressure, and said method comprising the additional step of setting said predetermined pressure lower than said medication pumping pressure of said internal pump.

4. A method as claimed in claim 1 comprising the additional step of maintaining said predetermined pressure constant during introduction of said predetermined volume of liquid into said implanted catheter.

5. A device for measuring flow resistance in a catheter for use with an implanted medication infusion system having a medication reservoir and an internal pump for conveying medication from said reservoir via a catheter to a selected site within a patient, said catheter being connected to an output of said internal pump via a one-way valve, and said system including a rinsing input for providing access to said catheter, said rinsing input being disposed upstream of said catheter and downstream of said internal pump, said device comprising:

means for percutaneously introducing a predetermined volume of liquid into said implanted catheter from an external syringe via said rinsing input at a predetermined pressure; and measuring means for measuring the time required for all of said volume of liquid to pass from said syringe through said implanted catheter via said rinsing input.

6. A device as claimed in claim 5 wherein said internal pump conveys said medication from said reservoir through said implanted catheter at a medication pumping pressure, and wherein said means for introducing said volume of liquid comprises means for introducing said volume of liquid at a predetermined pressure which is less than said medication pumping pressure of said internal pump.

7. A device as claimed in claim 5 wherein said means for introducing said volume of liquid into said implanted catheter via said rinsing input includes an extracorporeal connecting line and cannula percutaneously insertable into said rinsing input, said connecting line and said cannula having dimensions which do not significantly alter said time measured by said measuring means.

8. A device as claimed in claim 5 wherein said syringe has a plunger and wherein said means for introducing includes a fixture holding said syringe immobile and piston means operated by a compressible spring for acting on and displacing said plunger causing said predetermined volume of liquid to be expelled through said rinsing input and through said implanted catheter.

9. A device as claimed in claim 8 wherein said piston assumes an initial position before expressing said volume of liquid and wherein said piston assumes a final position at which said volume of liquid has been expressed, and wherein said measuring means comprises first signal generating means for generating a signal when said piston leaves said initial position and second signal generating means for generating a signal when said piston reaches said final position.

10. A device as claimed in claim 5 wherein said rinsing input is covered by a septum and wherein said means for introducing includes a cannula for penetrating through said septum, and said device further comprising pressure transducer means for indicating when said cannula has penetrated through said septum.

11. A device as claimed in claim 10 wherein said pressure transducer means comprises a pump stroke indicator means for sensing pump strokes of said internal pump.

* * * * *